(12) United States Patent
Jang et al.

(10) Patent No.: US 10,779,950 B2
(45) Date of Patent: Sep. 22, 2020

(54) KNEE JOINT IMPLANT PREVENTING HYPEREXTENSION

(71) Applicant: CORENTEC CO. LTD., Cheonan-si, Chungcheongnam-do (KR)

(72) Inventors: Young-Woong Jang, Seoul (KR); Chan-Eol Kim, Seoul (KR); Jae-Hun Ro, Seoul (KR); Ah-Reum Han, Gangwon-do (KR); Myung-Chul Lee, Gyeonggi-do (KR); Yong In, Seoul (KR); Seung-Beon Han, Seoul (KR)

(73) Assignee: Corentec Co. Ltd., Chungcheongnam-do (KR)

( * ) Notice: Subject to any disclaimer, the term of this patent is extended or adjusted under 35 U.S.C. 154(b) by 63 days.

(21) Appl. No.: 16/233,557

(22) Filed: Dec. 27, 2018

(65) Prior Publication Data
US 2020/0046507 A1 Feb. 13, 2020

(30) Foreign Application Priority Data
Aug. 8, 2018 (KR) .......................... 10-2018-0092366

(51) Int. Cl.
A61F 2/38 (2006.01)
A61F 2/30 (2006.01)
A61F 2/46 (2006.01)

(52) U.S. Cl.
CPC ............ *A61F 2/385* (2013.01); *A61F 2/3877* (2013.01); *A61F 2/389* (2013.01); *A61F 2/3859* (2013.01); *A61F 2/3886* (2013.01); *A61F 2/461* (2013.01); *A61F 2002/30001* (2013.01)

(58) Field of Classification Search
CPC .......... A61F 2/38; A61F 2/3859; A61F 2/385; A61F 2/3886; A61F 2/3877
See application file for complete search history.

(56) References Cited

U.S. PATENT DOCUMENTS

2013/0006373 A1* 1/2013 Wyss .................... A61F 2/3886
623/20.27

FOREIGN PATENT DOCUMENTS

KR 10-1184905 A 9/2012

\* cited by examiner

*Primary Examiner* — Jason-Dennis N Stewart
(74) *Attorney, Agent, or Firm* — Workman Nydegger

(57) ABSTRACT

A knee joint implant that prevents hyperextension includes a femoral component having an anterior surface with reference to the lowermost point of a convex condyle, the anterior surface being configured to have different curvature radii in respective sections thereof, and a bearing component having an anterior surface with reference to the lowermost point of a concave articular surface, the anterior surface being configured to have different curvature radii in respective sections, so that when an extended knee is about to be hyperextended, the convex condyle of the femoral component slides toward the anterior side and is brought into contact with a plurality of points of the concave articular surface of the bearing component, thereby producing resistance so as to suppress hyperextension exceeding a design range due to behavioral habits, a decrease in muscle mass, and the like of the patient.

11 Claims, 12 Drawing Sheets

KNEE JOINT IMPLANT PREVENTING HYPEREXTENSION

CROSS-REFERENCE TO RELATED APPLICATIONS

This application claims priority to Korean Application No. 10-2018-0092366, filed Aug. 8, 2018, the entire contents of which is incorporated herein by specific reference.

BACKGROUND OF THE INVENTION

1. Field of the Invention

The present disclosure relates to a knee joint implant that prevents hyperextension, and more particularly to a knee joint implant that prevents hyperextension, in which the knee joint implant includes a femoral component having an anterior surface with reference to the lowermost point of a convex condyle, the anterior surface being configured to have different curvature radii in respective sections thereof, and a bearing component having an anterior surface with reference to the lowermost point of a concave articular surface, the anterior surface being configured to have different curvature radii in respective sections, so that when an extended knee is about to be hyperextended, the convex condyle of the femoral component slides toward the anterior side and is brought into contact with a plurality of points of the concave articular surface of the bearing component, thereby generating resistive force so as to suppress hyperextension exceeding a design range due to behavioral habits, a decrease in muscle mass, and the like of the patient.

2. Description of the Prior Art

A knee joint is a joint formed by a femur, a tibia, and a patella, which are the three bones surrounding the knee, and corresponds to a key joint that supports the weight of a person and that is involved in exercising using the legs, such as walking or running through joint exercises.

Articular cartilage is present at the tip of the femur, and a meniscus is present at the tip of the tibia. When the cartilage is damaged due to extreme exercise, aging, or the like, bone and bone may come into direct contact with each other, which causes severe pain.

There has been proposed a total knee replacement (TKR) operation as an orthopedic treatment method when the above-mentioned damage occurs, in which an implant that can replace a damaged knee is inserted into a patient's bone.

FIG. 1 is a view showing a conventional artificial knee joint, and the conventional art is disclosed in Korean Patent No. 10-1184905 (Sep. 20, 2012). Now, descriptions will be made with reference to FIG. 1.

The TKR operation is an operation in which, when a knee joint is damaged, a femur F and a tibia T are partially incised and an artificial knee joint implant is implanted at the incision site. The artificial knee joint implant implantation procedure is performed in the manner of: fixing a femoral component 91 to a distal portion of the femur, fixing a tibial component 93 to a proximal portion of the tibia, and fixing a bearing component 95 between the femoral component 91 and the tibial component 93.

One of the problems with the TKR operation is that the knee is hyperextended in a patient who has undergone the TKR operation and eventually genu recurvatum (backknee), which is a symptom in which the knee joint is excessively bent backwards, occurs.

FIG. 2 illustrates a normal knee and a knee suffering from genu recurvatum for comparison therebetween. Referring to FIG. 2, the left side of FIG. 2 shows the state of a normal knee, and the right side of FIG. 2 shows the state of genu recurvatum, in which the distal end of the femur and the proximal end of the tibia are excessively moved backwards in the posterior direction.

After the TKR operation, the genu recurvatum resulting from hyperextension was found mainly in patients with weak muscles or poor walking habits, especially in elderly patients with severe aging of muscles, ligaments, or the like. Thus, weak muscles may cause problems.

This problem may also be caused by problems in terms of the shape of the femoral component and the bearing component used in the conventional TKR operation.

FIG. 3 is a view showing a single-point junction between a conventional femoral component and a bearing component in an extended state. As illustrated in FIG. 3, according to the conventional implant configuration, the convex condyle of the femoral component and the concave articular surface of the bearing component in the extended state are in single-point contact with each other on a sulcus point P, which is the lowermost point of a curved surface.

The single-point contact on the sulcus point causes movement of the femoral component that tilts toward the anterior side in the extended state.

Even with the single-point contact on the sulcus point, the problem of hyperextension may not occur when the muscles around the bones, ligaments, etc. strongly hold the bones that are liable to be dislocated. However, in the case of elderly patients with weak muscles and ligaments, the strength of the muscles and ligaments may be insufficient and thus the knees may be inevitably hyperextended.

As shown in FIG. 4, an elderly patient's knee having undergone TKR operation is tilted to the region in which the condyle of the femoral component is in contact with the anterior articular surface of the bearing component and thus the knee is afflicted with genu recurvatum, in which the knee is moved backwards in the state in which the patient stands upright.

Therefore, in the related art, it is required to introduce a new technique to prevent hyperextension through the structural shape of a knee joint implant itself even in the case of patients with weak muscles such as elderly people.

PRIOR ART DOCUMENT

Patent Document (Patent Document 1) Korean Patent No. 10-1184905 (published on Sep. 20, 2012)

SUMMARY OF THE INVENTION

The present disclosure has been conceived in order to solve the problems described above.

An aspect of the present disclosure is to provide a knee joint implant, in which, in the state in which a knee is extended, the femoral component having a convex condyle slides and a plurality of contact points are provided on the bearing component having a concave articular surface, whereby even if an elderly patient having aged muscles and ligaments undergoes a TKR operation, the occurrence of a hyperextension phenomenon can be suppressed.

Another aspect of the present disclosure is to provide a knee joint implant, in which the femoral component is configured to have a substantially flat shape in a predetermined region in the anterior direction from the lowermost point of the convex condyle thereof so as to solve a problem of hyperextension, which is caused as the convex condyle of the femoral component tilts to the front side of a contact point due to low muscle strength when the convex condyle of the femoral component is in single-point contact with the concave articular surface of the bearing component, by making the convex condyle of the femoral component and the concave articular surface of the bearing component come into two-point contact with each other, so that the occurrence of hyperextension of the knee can be suppressed by the structural shape of the implant even if muscle strength or the like is not applied thereto.

Another aspect of the present disclosure is to provide a knee joint implant, in which a convex condyle of a femoral component has a plurality of curvature radii at the anterior side thereof with respect to the lowermost point thereof, and a concave articular surface of a bearing component, which corresponds to the convex condyle, has a plurality of curvature radii at the anterior side thereof with respect to the lowermost point thereof such that the condyle and the articular surface do not have circumferential surface shapes that change abruptly, whereby the implant requires more force to cause hyperextension than an implant having a simple radius of curvature.

Another aspect of the present disclosure is to provide a knee joint implant in which a particular geometrical feature is imparted to the portion of the implant that performs joint motion such that when anatomical movement, which tends to go beyond a predetermined boundary region, is about to occur, resistive force against the anatomical movement itself can be generated due to the geometrical feature of the implant even without the help of surrounding muscles, ligaments, and the like.

Another aspect of the present disclosure is to provide a knee joint implant in which, even if the curvature radii in respective sections of the condyle of the femoral component are different from each other, the curvature radii in respective sections of the condyle are set to be smaller than the curvature radii in respective sections of the articular surface of the bearing component so as to solve a problem of increasing abrasion due to tight coupling since there is no marginal tolerance when the curvature radii are the same and so as to provide a stable margin such that the convex condyle of the femoral component is capable of easily performing joint motion on the concave articular surface of the bearing component.

Another aspect of the present disclosure is to provide a knee joint implant, in which the second curvature radius of the second section of the femoral component is set to be smaller than the first curvature radius of the first section such that a patient's normal anatomical shape can be reflected in the second section of the femoral component.

Another aspect of the present disclosure is to provide a knee joint implant, in which the third curvature radius of the third section of the femoral component is set to be smaller than the first curvature radius of the first section and larger than the second curvature radius of the second section such that when the extended knee is about to be hyperextended, the condyle of the femoral component slides on the bearing component and then comes into two-point contact with the bearing component, thereby preventing further hyperextension.

Another aspect of the present disclosure is to provide a knee joint implant, in which the first angle of the condyle of the femoral component is set to be smaller than the second angle such that the section in which the condyle of the femoral component slides on the articular surface of the bearing component is minimized, thereby preventing the patient's behavior itself from becoming unnatural.

Another aspect of the present disclosure is to provide a knee joint implant, in which the bearing component has a substantially flat shape in a predetermined region in the anterior direction from the lowermost point of the concave articular surface so as to allow the first section of the femoral component, which is substantially flat, to be seated on the predetermined region such that when the extended knee is about to be hyperextended, the first section of the femoral component slides on the fourth section of the bearing component and then comes into two-point contact with the fourth section, thereby preventing hyperextension.

Another aspect of the present disclosure is to provide a knee joint implant, in which the fifth curvature radius of the fifth section of the bearing component is set to be smaller than the fourth curvature radius of the fourth section such that a patient's normal anatomical shape can be reflected in the fifth section of the bearing component.

Another aspect of the present disclosure is to provide a knee joint implant, in which the sixth curvature radius of the sixth section of the bearing component is set to be smaller than the fourth curvature radius of the fourth section and larger than the fifth curvature radius of the fifth section such that when the extended knee is about to be hyperextended, the condyle of the femoral component slides on the bearing component and then comes into two-point contact with the bearing component, thereby preventing further hyperextension.

Still another aspect of the present disclosure is to provide a knee joint implant, in which the fourth angle of the bearing component is set to be smaller than the fifth angle such that the section in which the condyle of the femoral component slides on the articular surface of the bearing component is minimized, thereby preventing the patient's behavior itself from becoming unnatural.

Yet another aspect of the present disclosure is to provide a knee joint implant, in which the area of the first section is set to be smaller than the area of the fourth section such that the first section of the femoral component is capable of sliding more stably on the fourth section of the bearing component.

In view of the above aspects of the present disclosure, the present disclosure is implemented by embodiments having the configurations as follows.

According to an embodiment of the present disclosure, a knee joint implant includes a femoral component having an anterior surface with reference to a lowermost point of a convex condyle, the anterior surface being configured to have different curvature radii in respective sections thereof. When an extended knee is about to be hyperextended, the condyle of the femoral component slides toward an anterior side along a concave articular surface of a bearing component and is then brought into contact with the articular surface at a plurality of points.

According to another embodiment of the present disclosure, the femoral component includes a first section having a first curvature radius from the lowermost point of the condyle and extending toward the anterior side by a first angle from a center of the first curvature radius.

According to another embodiment of the present disclosure, the femoral component includes a second section having a second curvature radius from an end of the first section and extending toward the anterior side by a second angle from a center of the second curvature radius, and a third section having a third curvature radius from an end of the second section and extending toward the anterior side by a third angle from a center of the third curvature radius, and the points, which are brought into contact with the articular surface when the extended knee is about to be hyperextended, are formed in the first section and the third section.

According to another embodiment of the present disclosure, the first curvature radius is larger than the second curvature radius.

According to another embodiment of the present disclosure, the third curvature radius is smaller than the first curvature radius and larger than the second curvature radius.

According to another embodiment of the present disclosure, the first angle is smaller than the second angle.

According to another embodiment of the present disclosure, the knee joint implant includes a bearing component having an anterior surface with reference to a lowermost point of a concave articular surface, the anterior surface being configured to have different curvature radii in respective sections thereof. When an extended knee is about to be hyperextended, the bearing component is brought into contact with a condyle of the femoral component, which slides toward an anterior side along a concave articular surface of the bearing component, at a plurality of points.

According to another embodiment of the present disclosure, the bearing component includes a fourth section having a fourth curvature radius from the lowermost point of the articular surface and extending toward the anterior side by a fourth angle from the center of the fourth curvature radius.

According to another embodiment of the present disclosure, the bearing component includes a fifth section having a fifth curvature radius from an end of the fourth section and extending toward the anterior side by a fifth angle from a center of the fifth curvature radius, and a sixth section, having a sixth curvature radius from an end of the fifth section and extending toward the anterior side by a sixth angle from a center of the sixth curvature radius, and the points, which are brought into contact with the condyle when the extended knee is about to be hyperextended, are formed in the fourth section and the sixth section.

According to another embodiment of the present disclosure, the fourth curvature radius is larger than the fifth curvature radius.

According to another embodiment of the present disclosure, the sixth curvature radius is smaller than the fourth curvature radius and larger than the fifth curvature radius.

According to another embodiment of the present disclosure, the fourth angle is smaller than the fifth angle.

According to another embodiment of the present disclosure, a knee joint implant includes a femoral component having an anterior surface with reference to a lowermost point of a convex condyle, the anterior surface being configured to have different curvature radii in respective sections thereof, and a bearing component having an anterior surface with reference to a lowermost point of a concave articular surface, the anterior surface being configured to have different curvature radii in respective sections thereof. The femoral component and the bearing component are configured such that, when an extended knee is about to be hyperextended, the condyle slides toward an anterior side along a concave articular surface of a bearing component and is then brought into contact with the articular surface at a plurality of points.

According to another embodiment of the present disclosure, the femoral component includes a first section having a first curvature radius from the lowermost point of the condyle and extending toward the anterior side by a first angle from a center of the first curvature radius, and the bearing component includes a fourth section having a fourth curvature radius from the lowermost point of the articular surface and extending toward the anterior side by a fourth angle from the center of the fourth curvature radius.

According to another embodiment of the present disclosure, the femoral component includes a second section having a second curvature radius from an end of the first section and extending toward the anterior side by a second angle from a center of the second curvature radius, and a third section having a third curvature radius from an end of the second section and extending toward the anterior side by a third angle from a center of the third curvature radius, and the bearing component includes a fifth section having a fifth curvature radius from an end of the fourth section and extending toward the anterior side by a fifth angle from a center of the fifth curvature radius, and a sixth section having a sixth curvature radius from an end of the fifth section and extending toward the anterior side by a sixth angle from a center of the sixth curvature radius. When the extended knee is about to be hyperextended, each of the first and fourth sections and the third and sixth sections forms a contact point.

According to another embodiment of the present disclosure, the first curvature radius is smaller than the fourth curvature radius, the second curvature radius is smaller than the fifth curvature radius, and the third curvature radius is smaller than the sixth curvature radius.

According to another embodiment of the present disclosure, the first section has an area that is smaller than the area of the fourth section.

The present disclosure is capable of obtaining the following effects through a combination the above-described embodiment and the configurations to be described below and a use relationship therebetween.

The present disclosure provides a knee joint implant, in which, in the state in which a knee is extended, a femoral component having a convex condyle slides and a plurality of contact points are provided on a bearing component having a concave articular surface. Thus, even if an elderly patient having aged muscles and ligaments undergoes a TKR operation, the occurrence of a hyperextension phenomenon can be suppressed.

The present disclosure provides a knee joint implant, in which a femoral component is configured to have a substantially flat shape in a predetermined region in an anterior direction from the lowermost point of a convex condyle thereof so as to solve a problem of hyperextension, which is caused as the convex condyle of the femoral component tilts to the front side of a contact point due to low muscle strength when the convex condyle of the femoral component is in single-point contact with a concave articular surface of a bearing component, by making the convex condyle of the femoral component and the concave articular surface of the bearing component come into two-point contact with each other. Thus, it is possible to suppress the occurrence of hyperextension of the knee using the structural shape of the implant even if muscle strength or the like is not applied thereto.

The present disclosure provides a knee joint implant, in which a convex condyle of a femoral component has a plurality of curvature radii at the anterior side thereof with respect to the lowermost point thereof, and a concave articular surface of a bearing component, which corresponds to the convex condyle, has a plurality of curvature radii at the anterior side thereof with respect to the lowermost point thereof such that the condyle and the articular surface do not have circumferential surface shapes that change abruptly.

Thus, the implant requires more force than an implant having a simple curvature radius in order to cause hyperextension.

The present disclosure provides a knee joint implant, in which a particular geometrical feature is imparted to the portion of the implant that performs joint motion. Thus, when anatomical movement, which tends to go beyond a predetermined boundary region, is about to occur, resistive force against the anatomical movement itself can be generated due to the geometrical feature of the implant even without the help of surrounding muscles, ligaments, and the like.

The present disclosure provides a knee joint implant, in which, even if the curvature radii in respective sections of the condyle of the femoral component are different from each other, the curvature radii in respective sections of the condyle are set to be smaller than the curvature radii in respective sections of the articular surface of the bearing component so as to solve a problem of increasing abrasion due to tight coupling since there is no marginal tolerance and so as to provide a stable margin such that the convex condyle of the femoral component is capable of easily performing joint motion on the concave articular surface of the bearing component.

The present disclosure provides a knee joint implant, in which the second curvature radius of the second section of the femoral component is set to be smaller than the first curvature radius of the first section such that a patient's normal anatomical shape can be reflected in the second section of the femoral component.

The present disclosure provides a knee joint implant, in which the third curvature radius of the third section of the femoral component is set to be smaller than the first curvature radius of the first section and larger than the second curvature radius of the second section such that, when the extended knee is about to be hyperextended, the condyle of the femoral component slides on the bearing component and then comes into two-point contact with the bearing component, thereby preventing further hyperextension.

The present disclosure provides a knee joint implant, in which the first angle of the condyle of the femoral component is set to be smaller than the second angle such that the section in which the condyle of the femoral component slides on the articular surface of the bearing component is minimized, thereby preventing the patient's behavior itself from becoming unnatural.

The present disclosure provides a knee joint implant, in which the bearing component has a substantially flat shape in a predetermined region in the anterior direction from the lowermost point of the concave articular surface so as to allow the first section of the femoral component, which is substantially flat, to be seated on the predetermined region such that when the extended knee is about to be hyperextended, the first section of the femoral component slides on the fourth section of the bearing component and then comes into two-point contact with the fourth section, thereby preventing hyperextension.

The present disclosure provides a knee joint implant, in which the fifth curvature radius of the fifth section of the bearing component is set to be smaller than the fourth curvature radius of the fourth section such that a patient's normal anatomical shape can be reflected in the fifth section of the bearing component.

The present disclosure provides a knee joint implant, in which the sixth curvature radius of the sixth section of the bearing component is set to be smaller than the fourth curvature radius of the fourth section and larger than the fifth curvature radius of the fifth section such that when the extended knee is about to be hyperextended, the condyle of the femoral component slides on the bearing component and then comes into two-point contact with the bearing component, thereby preventing further hyperextension.

The present disclosure provides a knee joint implant, in which the fourth angle of the bearing component is set to be smaller than the fifth angle such that the section in which the condyle of the femoral component slides on the articular surface of the bearing component is minimized, thereby preventing the patient's behavior itself from becoming unnatural.

The present disclosure provides a knee joint implant, in which the area of the first section is set to be smaller than the area of the fourth section such that the first section of the femoral component is capable of sliding more stably on the fourth section of the bearing component.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, embodiments of a knee joint implant that prevents hyperextension according to the present disclosure will be described in detail with reference to the accompanying drawings. In the following description of the present disclosure, a detailed description of known functions or configurations will be omitted when it is determined that the detailed description may make the subject matter of the present disclosure rather unclear. Unless defined otherwise, all terms used herein have the same meanings as general meanings of terms understood by a person ordinarily skilled in the art to which this disclosure belongs, and when the general meanings conflict with the meanings of the terms used herein, the meanings of the terms follow the definition used in the specification.

In this specification, the drawings are illustrated on the basis of a knee joint implant to be inserted into a left knee of a patient.

Figure 1:
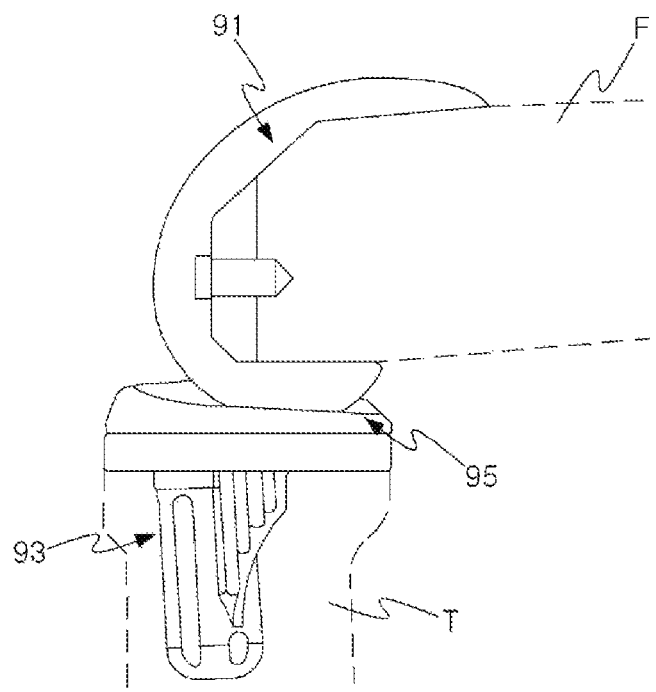
FIG. 1 is a view showing a conventional artificial knee joint.
Figure 2:
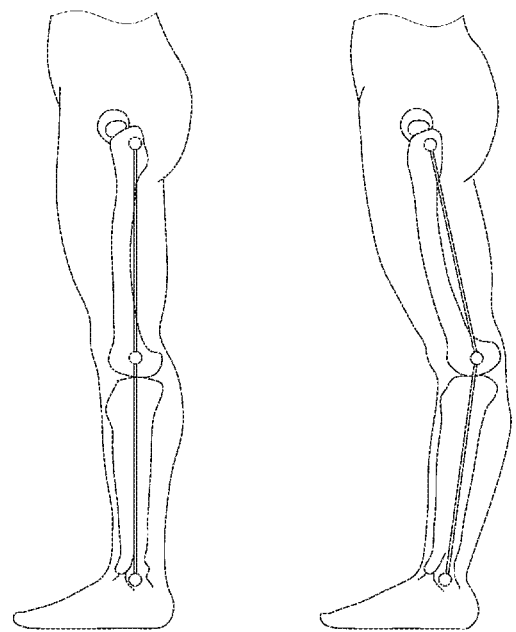
FIG. 2 is a view showing a normal knee and a knee afflicted with genu recurvatum.
Figure 3:
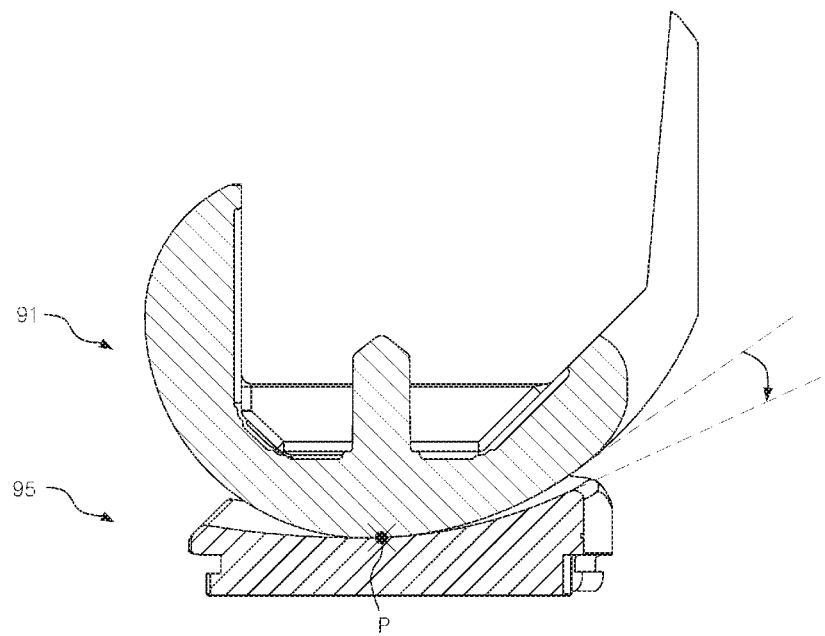
FIG. 3 is a view showing a single-point junction between a femoral component and a bearing component of the prior art in an extended state.
Figure 4:
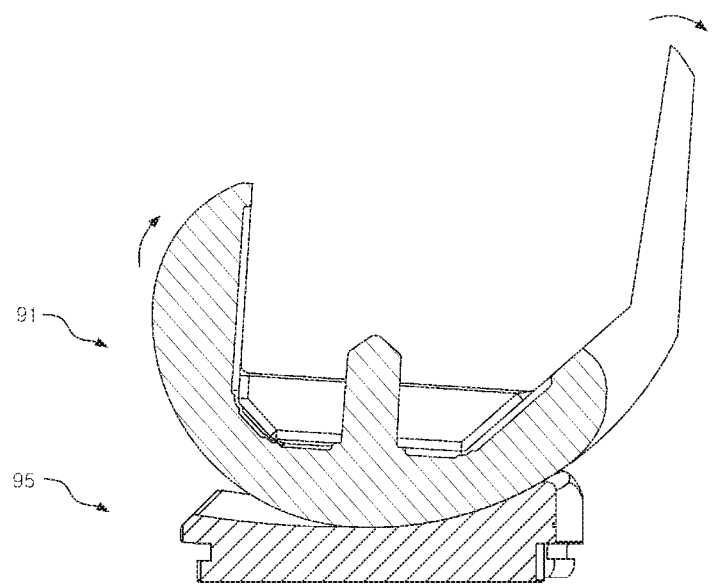
FIG. 4 is a view showing the implant of FIG. 3 in the state of being hyperextended.
Figure 5:
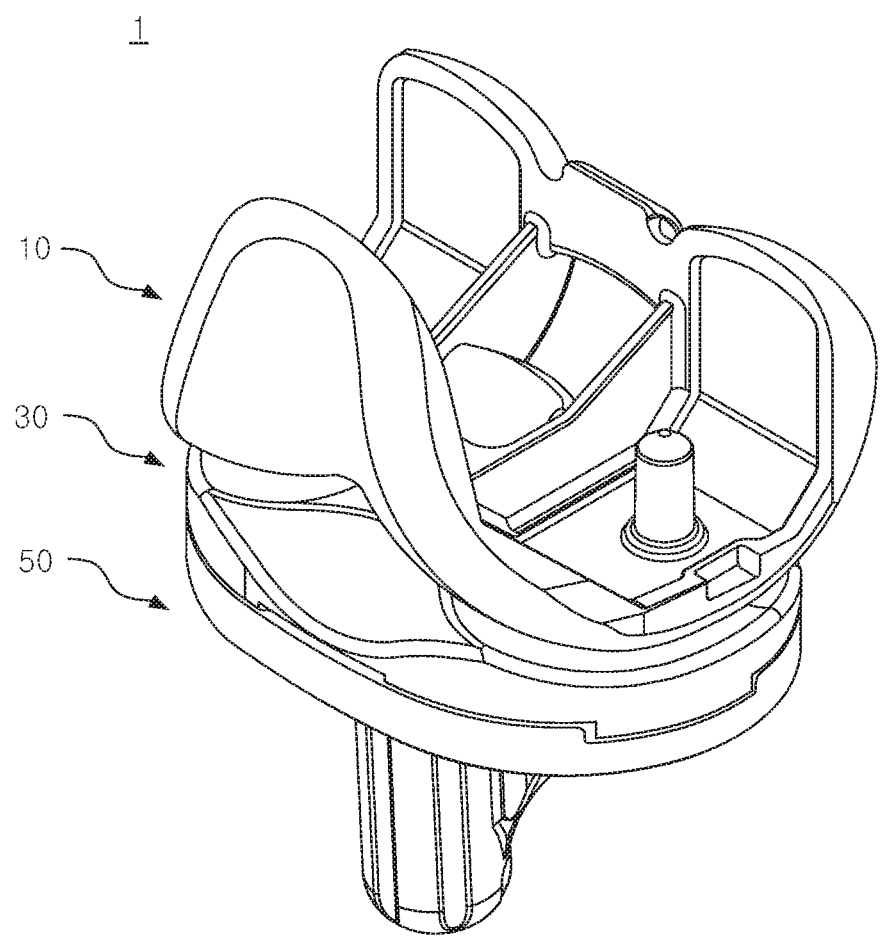
FIG. 5 is a perspective view illustrating a knee joint implant according to an embodiment of the present disclosure.
Figure 6:
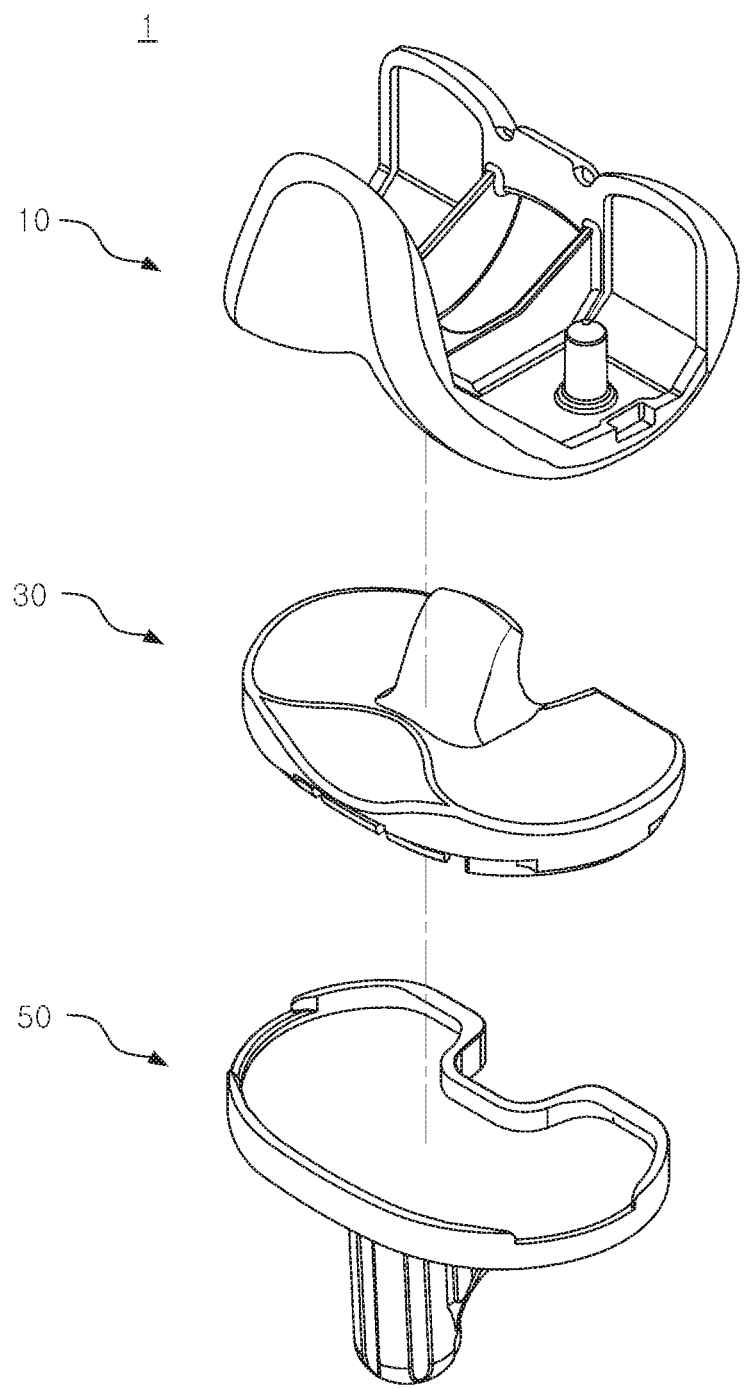
FIG. 6 is an exploded perspective view of FIG. 5.

FIG. 5 is a perspective view illustrating a knee joint implant according to an embodiment of the present disclosure, and FIG. 6 is an exploded perspective view of FIG. 5. Referring to FIGS. 5 and 6, a knee joint implant 1 that prevents hyperextension according to the present disclosure is an implant used in a TKR operation, and is preferably inserted into the distal portion of a femur and a proximal portion of a tibia or between the distal portion of the femur and the proximal portion of the tibia. Specifically, as illustrated in FIGS. 5 and 6, the knee joint implantation 10 includes a femoral component 10, a bearing component 30, and a tibial component 50.

Figure 7:
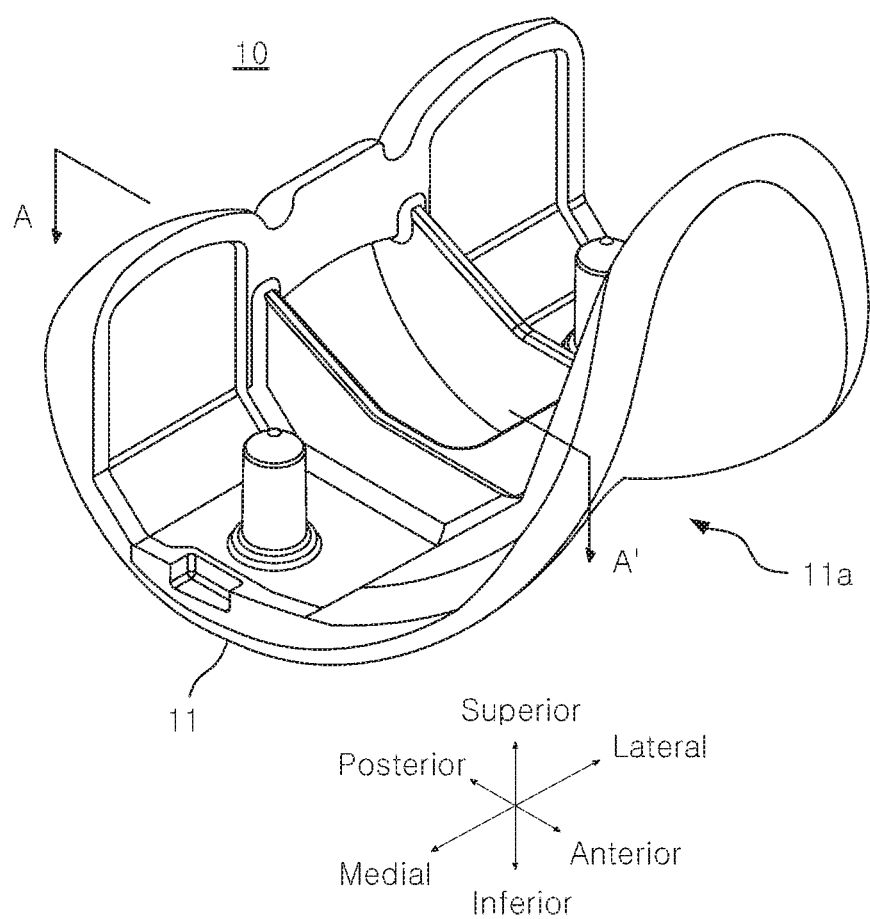
FIG. 7 is a perspective view illustrating a femoral component according to an embodiment of the present disclosure.

FIG. 7 is a perspective view illustrating a femoral component according to an embodiment of the present disclosure. Referring to FIG. 7, the femoral component 10 refers to an implant inserted into a distal portion of the femur after partially incising the convex distal end of the femur so as to replace the incised portion. The femoral component 10 may be configured such that the anterior surface 11a with reference to the lowermost point 111 of the convex condyle 11, to be described later, has different curvature radii in respective sections thereof. Even when an elderly patient having aged muscles or ligaments undergoes a TKR operation, when the extended knee is about to be hyperextended due to an action of descending stairs or the like, through the different curvature radii, the condyle 11, to be described later, slides toward the anterior side along the concave articular surface 31 of the bearing component 30, to be described later, and is then brought into contact with the articular surface 31 at a plurality of points, so that the occurrence of the hyperextension phenomenon can be prevented owing to the structural shape of the implant. The femoral component 10 includes a condyle 11.

Figure 8:
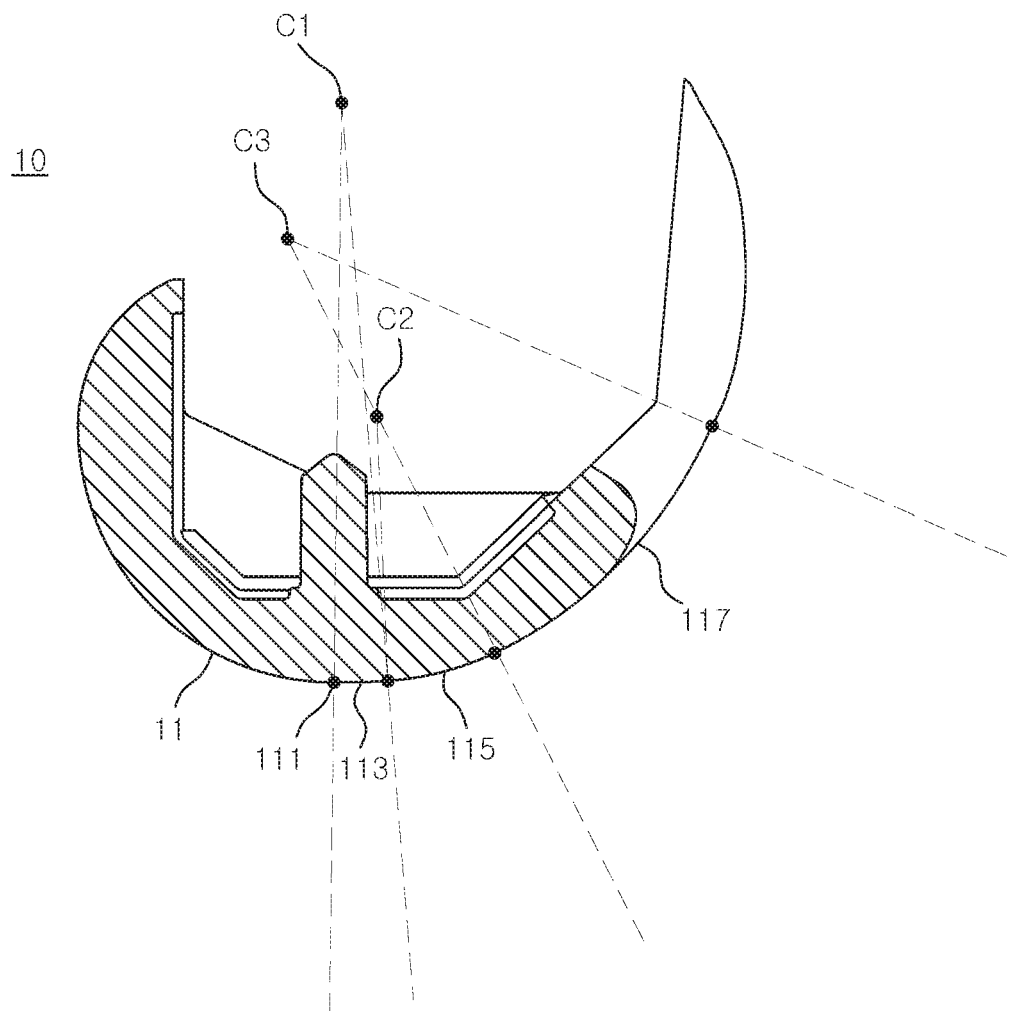
FIG. 8 is a cross-sectional view taken along line A-A' in FIG. 7.
Figure 9:
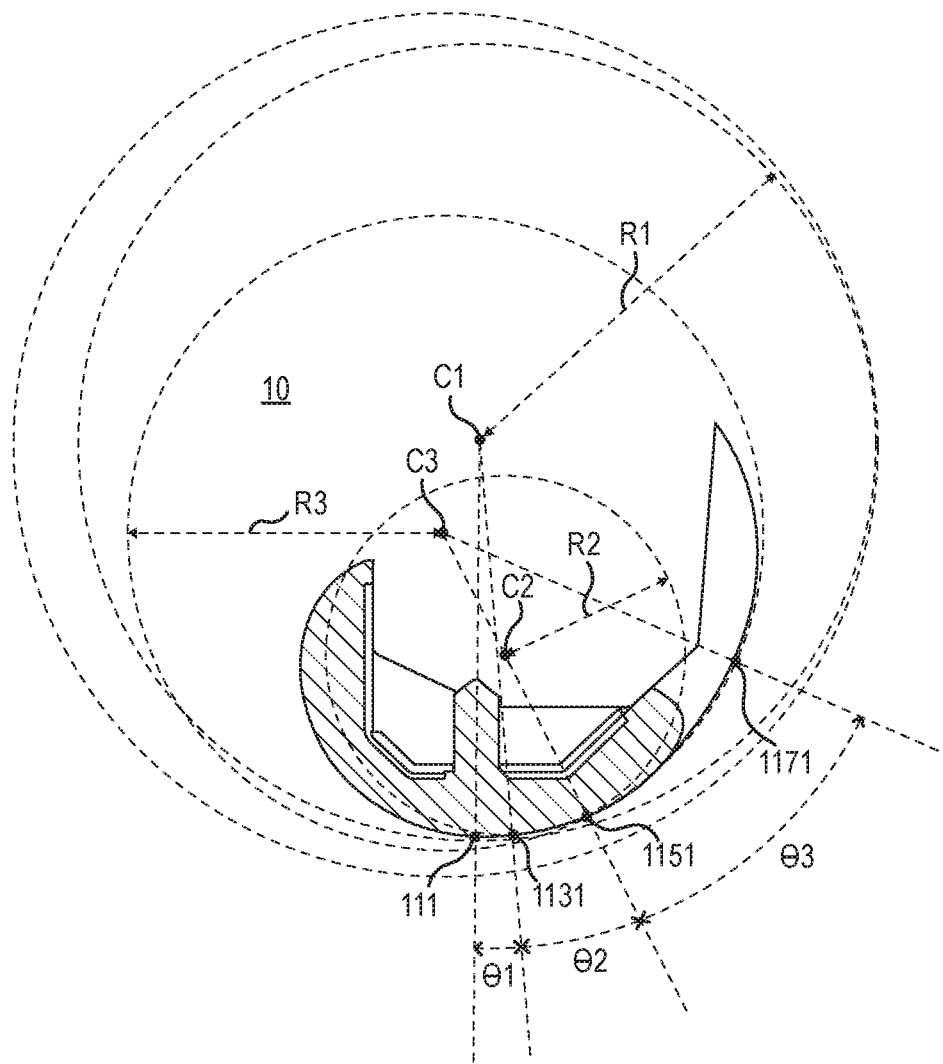
FIG. 9 is a view showing curvature radii and angles of respective sections in FIG. 8.

As illustrated in FIG. 7, the condyle 11 is a portion that is convex downwards in the femoral component 10, which is divided into a medial portion and a lateral portion. The condyle 11 is in contact with the articular surface of the bearing component 30, to be described later, so as to enable joint motion. FIG. 8 is a cross-sectional view taken along line A-A' in FIG. 7, and FIG. 9 is a view showing curvature radii and angles in respective sections in FIG. 8. Referring to FIGS. 8 and 9, the condyle 11 includes a lowermost point 111, a first section 113, a second section 115, and a third section 117.

The lowermost point 111 is a portion pointing to the lowest point of the curved surface of the femoral component 10. As shown in FIGS. 8 and 9, the lowermost point 111 is used to mean the lowest portion of the convexly curved surface in the condyle 11 of the femoral component 10, which is configured to be downwardly convex. The lowermost point 111 of the femoral component 10 may be configured to come into contact with the lowermost point 311 of the articular surface 31 of the bearing component 30, to be described later, in the extended state, in which the patient stands upright. The surface of the condyle 11 that is located at the anterior side with reference to the lowermost point 111 is referred to as an anterior surface 11a, and the present disclosure is characterized in that the anterior surface 11a has various curvature radii.

As illustrated in FIGS. 8 and 9, the first section 113 means a portion that has a first curvature radius R1 from the lowermost point 111 of the condyle 11 and extends toward the anterior side by a first angle θ1 from the center C1 of the first curvature radius R1. Preferably, the first section 113 may be configured to be substantially horizontal.

The first section 113 is a portion formed to be generally horizontal on the condyle 11, which has a convex shape as a whole, and allows the femoral component 10 to slide on the articular surface 31 of the bearing component 30, to be described later. The term "slide" means that the femoral component 10 slides toward the anterior side on the articular surface 31 of the bearing component 30, to be described later. The meaning of "slide" shall not be interpreted in a narrow sense as the translational movement of the femoral component 10 only, but is preferably interpreted to include the fact that predetermined rotational movement may accompany the translational movement.

As described above, the first section 113 guides sliding of the femoral component 10 on the bearing component 30. Since the behavior of the patient may be unnatural when the first section 113 is excessively long, it is preferable that the length of the first section 113 be minimized. Therefore, more preferably, the first angle θ1 may be set to be smaller than the second angle θ2, to be described later (θ1<θ2).

As will be described in detail later, in order to prevent the extended knee from being hyperextended due to an action of descending stairs or the like, the present disclosure constitutes two contact points, one of which is formed in the first section 113.

The first curvature radius R1 and the first angle θ1 of the first section 113 are not limited to any particular concept, but preferably, the first curvature radius R1 may be about 85 mm and the first angle θ1 may be about 11 degrees.

As illustrated in FIGS. 8 and 9, a second section 115 means a portion that has a second curvature radius R2 from an end 1131 of the first section 113 and extends toward the anterior side by a second angle θ2 from the center C2 of the second curvature radius R2.

The second section 115 is a portion that corresponds to a normal patient's anatomical shape. While the first section 113 is a substantially horizontal section, the second section 115 may have a curvature that changes somewhat abruptly since the normal patient's anatomical shape is implemented therein. Preferably, the second curvature radius R2 may be set to be smaller than the first curvature radius R1 (R1>R2) such that the second section 115 is not brought into contact with the articular surface 31 of the bearing component 30, to be described later, when the extended knee is about to be hyperextended.

In addition, when the length of the first section 113 configured to guide the sliding of the femoral component 10 increases, the behavior of the patient becomes unnatural and thus it is preferable that the length of the first section 113 be minimized. Thus, the second angle θ2 may be set to be larger than the first angle θ2 (θ2>θ1).

The second curvature radius R2 and the second angle θ2 of the second section 115 are not limited to any particular concept, but preferably, the second curvature radius R2 may be about 26.5 mm and the second angle θ2 may be about 14 degrees.

The third section 117 is a portion that has a third curvature radius R3 from an end 1151 of the second section 115 and extends toward the anterior side by a third angle θ3 from the center C3 of the third curvature radius R3 to the end 11171. A section having another curvature radius beyond the end 1171 of the third section 117 is formed, and is brought into contact with a patella implant (not shown). However, a description of the region beyond the end 1171 of the third section 117 is omitted.

In order to prevent the extended knee from being hyperextended due to an action of descending stairs or the like, the present disclosure preferably constitutes two contact points, one of which may be formed in the first section 113 and the remaining one of which may be formed in the third section 117. To this end, the third curvature radius R3 may be set to be smaller than the first curvature radius R1 and larger than the second curvature radius R2 (R1>R3>R2).

The third curvature radius R3 of the third section 117 is not limited to any particular concept, but preferably, the third curvature radius R3 may be about 38.5 mm.

Figure 10:
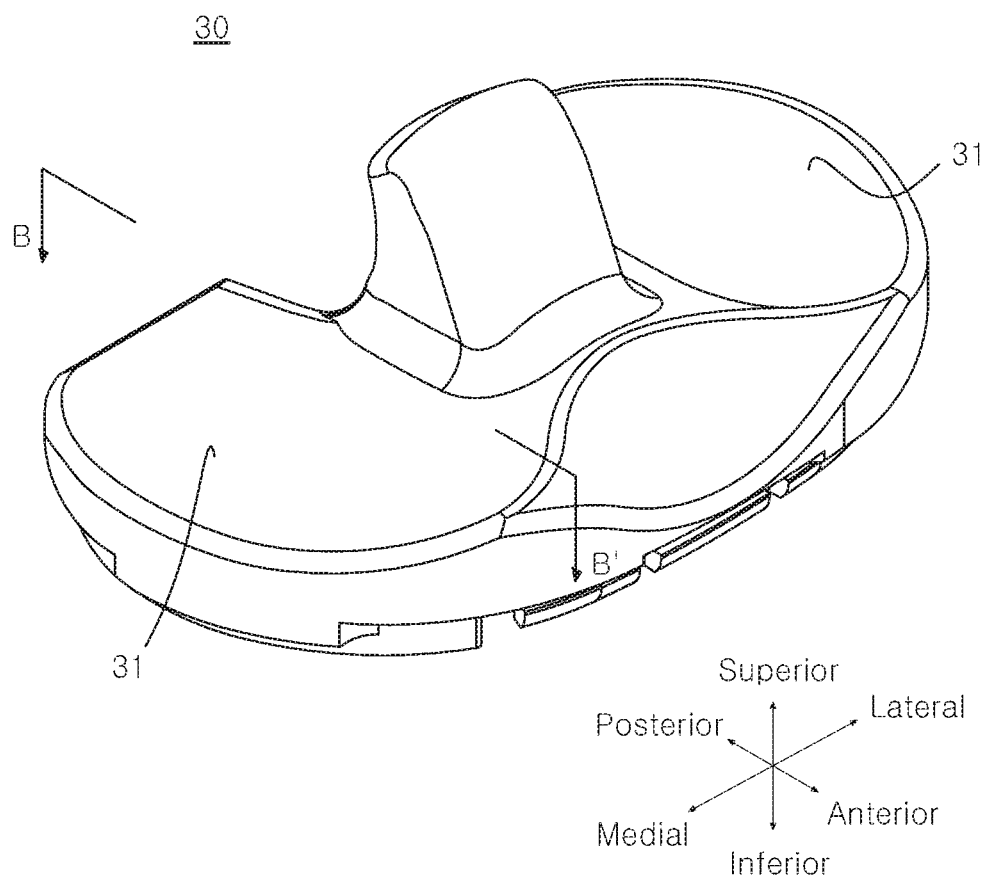
FIG. 10 is a perspective view illustrating a bearing component according to an embodiment of the present disclosure.

FIG. 10 is a perspective view illustrating a bearing component according to an embodiment of the present disclosure. Referring to FIG. 10, the bearing component 30 is a component that is brought into contact with the condyle 11 of the femoral component 10 by being seated on the tibial component 50 inserted into the proximal portion of the tibia after incising a predetermined portion from the proximal end of the tibia so as to replace the incised portion. The bearing component 30 may be configured such that the anterior surface 31a with reference to the lowermost point 311 of the concave articular surface 31, to be described later, has different curvature radii in respective sections thereof. Even when an elderly patient having aged muscles or ligaments undergoes a TKR operation, when the extended knee is about to be hyperextended due to an action of descending stairs or the like, through the different curvature radii, the condyle 11 slides toward the anterior side along the concave articular surface 31 of the bearing component 30 and is then brought into contact with the articular surface 31 at a plurality of points, so that occurrence of the hyperextension phenomenon can be prevented owing to the structural shape of the implant. The bearing component 30 includes a articular surface 31.

Figure 11:
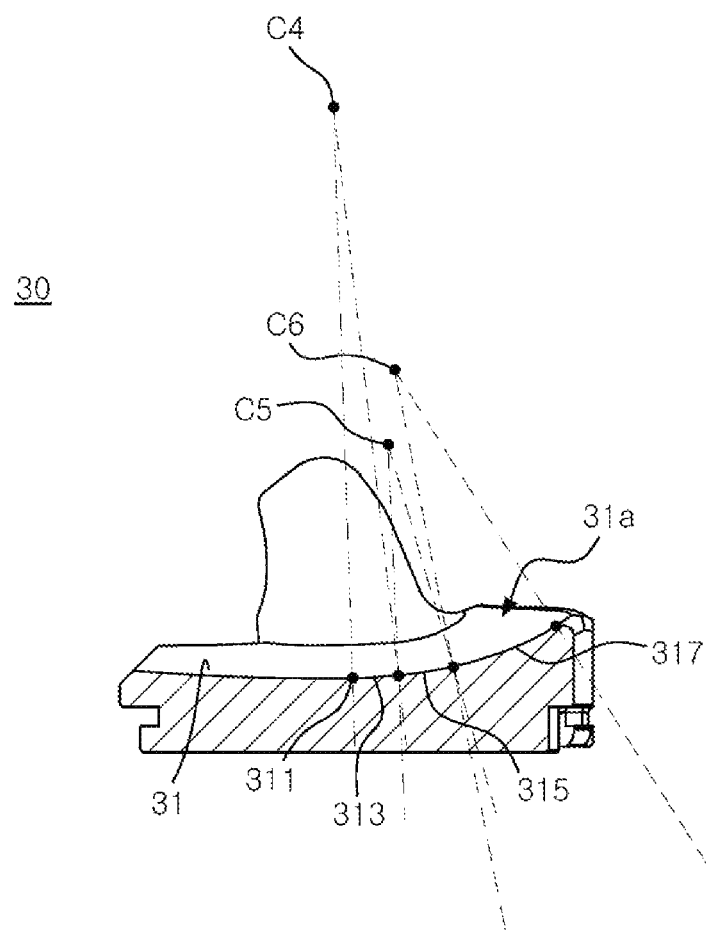
FIG. 11 is a cross-sectional view taken along line B-B' in FIG. 10.
Figure 12:
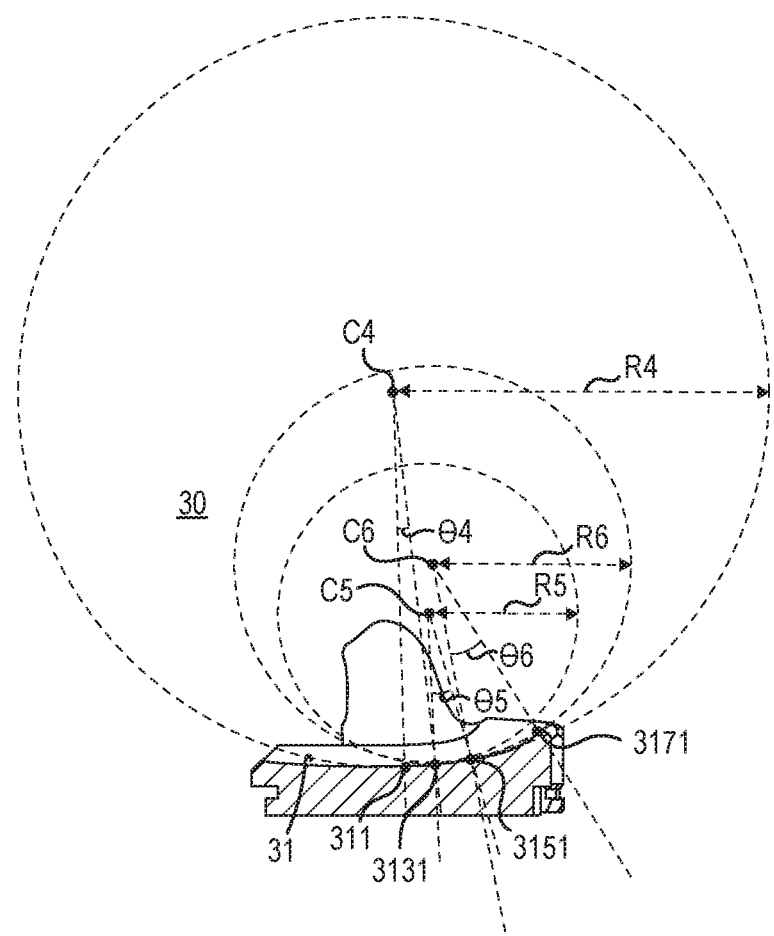
FIG. 12 is a view showing curvature radii and angles of respective sections in FIG. 11.

The articular surface 31 is a portion that is recessed downward in the bearing component 30, and is divided into a medial portion and a lateral portion, as shown in FIG. 10. The articular surface 31 is brought into contact with the convex condyle 11 of the femoral component 10 so as to enable joint motion. FIG. 11 is a cross-sectional view taken along line B-B' in FIG. 10, and FIG. 12 is a view showing curvature radii and angles in respective sections in FIG. 11. Referring to FIGS. 11 and 12, the articular surface 31 includes a lowermost point 311, a fourth section 313, a fifth section 315, and a sixth section 317.

The lowermost point 311 is the most deeply recessed portion in the curved surface of the concave articular surface 31 of the bearing component 30. As shown in FIGS. 11 and 12, the lowermost point 311 is the lowest point in the downwardly curved surface of the articular surface 31 of the bearing component 30. Preferably, the above-described lowermost point 111 of the femoral component 10 may be configured to come into contact with the lowermost point 311 of the bearing component 30 in the extended state, in which the patient stands upright. The surface of the articular surface 31, which is located at the anterior side with reference to the lowermost point 311, is referred to as an anterior surface 31a, and the present disclosure is characterized in that the anterior surface 31a has various curvature radii.

The fourth section 313 is a portion that has a fourth curvature radius R4 from the lowermost point 311 of the articular surface 31 and extends toward the anterior side by a fourth angle θ4 from the center C4 of the fourth curvature radius R4. Preferably, the fourth section 313 may be configured to be substantially horizontal. The fourth section 313 is a portion, on which the first section 113 configured to be substantially horizontal, is seated, and it is preferable that the area of the fourth section 313 be set to be larger than the area of the first section 113.

A point, which is brought into contact with the condyle 11 of the femoral component 10 when the extended knee is about to be hyperextended, may be formed in the fourth section 313. Preferably, the first section 113 of the condyle 11 and the fourth section 313 may form a contact point P.

In order for the condyle 11 of the femoral component 10 to be seated on the articular surface 31 of the bearing component 30 and to perform smooth joint motion, it is preferable that the curvature radii of respective sections of the condyle 11 be set to be smaller than the curvature radii of respective sections of the articular surface 31. When the curvature radii of respective sections of the articular surface 31 are equal to the curvature radii of respective sections of the condyle 11, abrasion of the implant may be facilitated because the condyle 11 and the articular surface 31 are tightly coupled, since there is no marginal tolerance. Consequently, it is preferable that the curvature radii of respective sections of the articular surface 31 of the bearing component be set to be larger than the curvature radii of respective sections of the condyle 11. Accordingly, the fourth curvature radius R4 may be set to be larger than the first curvature radius R1.

The fourth curvature radius R4 and the fourth angle θ4 of the fourth section 313 are not limited to any particular concept, but preferably, the fourth curvature radius R4 may be about 85.5 mm and the fourth angle θ4 may be about 5 degrees.

The fifth section 315 is a portion that has a fifth curvature radius R5 from an end 3131 of the fourth section 313 and extends toward the anterior side by a fifth angle θ5 from the center C5 of the fifth curvature radius R5.

The fifth section 315 is a portion that corresponds to a normal patient's anatomical shape while the fourth section 313 is a substantially horizontal section, and the fifth section 315 may have a curvature that somewhat abruptly changes since the normal patient's anatomical shape is reflected therein. Preferably, the fifth curvature radius R5 may be set to be smaller than the fourth curvature radius R4 (R4>R5) such that the fifth section 315 is not brought into contact with the condyle 11 when the extended knee is about to be hyperextended.

The fifth section 315 is a portion that corresponds to the second section 115 of the condyle 11. As described above, in order to ensure that the condyle 11 of the femoral component 10 performs smooth joint motion on the articular surface 31 of the bearing component 30, it is preferable that the fifth curvature radius R5 of the fifth section 315 be set to be larger than the second curvature radius R2 of the second section 115.

In addition, the fifth section 315 supports the sliding of the first section 113 of the femoral component 10, which is substantially horizontal. When the sliding section increases, the patient's behavior becomes unnatural. Thus, it is preferable that the fifth section 315 be minimized. Therefore, the fifth angle θ5 may be set to be larger than the fourth angle θ4 (θ5>θ4).

The fifth curvature radius R5 and the fifth angle θ5 of the fifth section 315 are not limited to any particular concept, but preferably, the fifth curvature radius R5 may be about 27 mm and the fifth angle θ5 may be about 9 degrees.

The sixth section 317 means a portion that has a sixth curvature radius R6 from an end 3151 of the fifth section 315 and extends toward the anterior side by a sixth angle θ6 from the center C6 of the sixth curvature radius R6. In order to prevent the extended knee from being hyperextended due to an action of descending stairs or the like, preferably, the present disclosure constitutes two contact points, one of which may be formed in the fourth section 313, and a remaining one of which may be formed in the sixth section 317. To this end, the sixth curvature radius R6 may be set to be smaller than the fourth curvature radius R4 and larger than the fifth curvature radius R5 (R4>R6>R5).

The first section 113 of the condyle 11 and the fourth section 313 of the articular surface 31, and the third section 117 of the condyle 11 and the sixth section 317 of the articular surface 31 form respective contact points P. In the knee joint implant 1 according to the present disclosure, when the extended knee is about to be hyperextended due to further extension of the extended knee in the process of descending stairs or the like, a plurality of contact points P are formed, thereby preventing hyperextension of the joint.

The sixth section 317 is a portion that corresponds to the third section 117 of the condyle 11. In order to ensure that the condyle 11 of the femoral component 10 performs smooth joint motion on the articular surface 31 of the bearing component 30, it is preferable that the sixth curvature radius R6 of the sixth section 317 be set to be larger than the third curvature radius R3 of the third section 117.

The sixth curvature radius R6 of the sixth section 317 is not limited to any particular concept, but preferably, the sixth curvature radius R6 may be about 39 mm.

Figure 13:
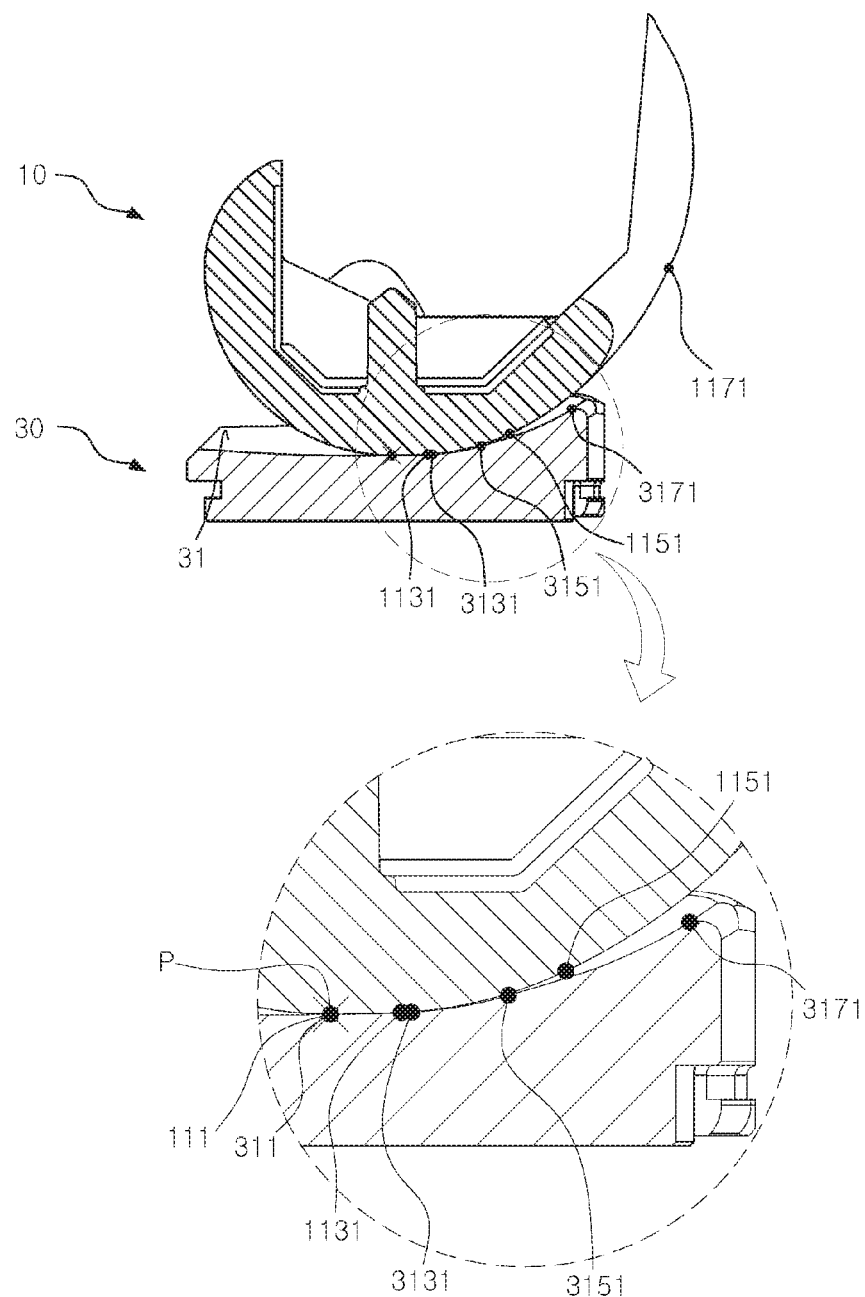
FIG. 13 is a view showing contact points in the extended state of a knee joint implant according to an embodiment of the present disclosure.
Figure 14:
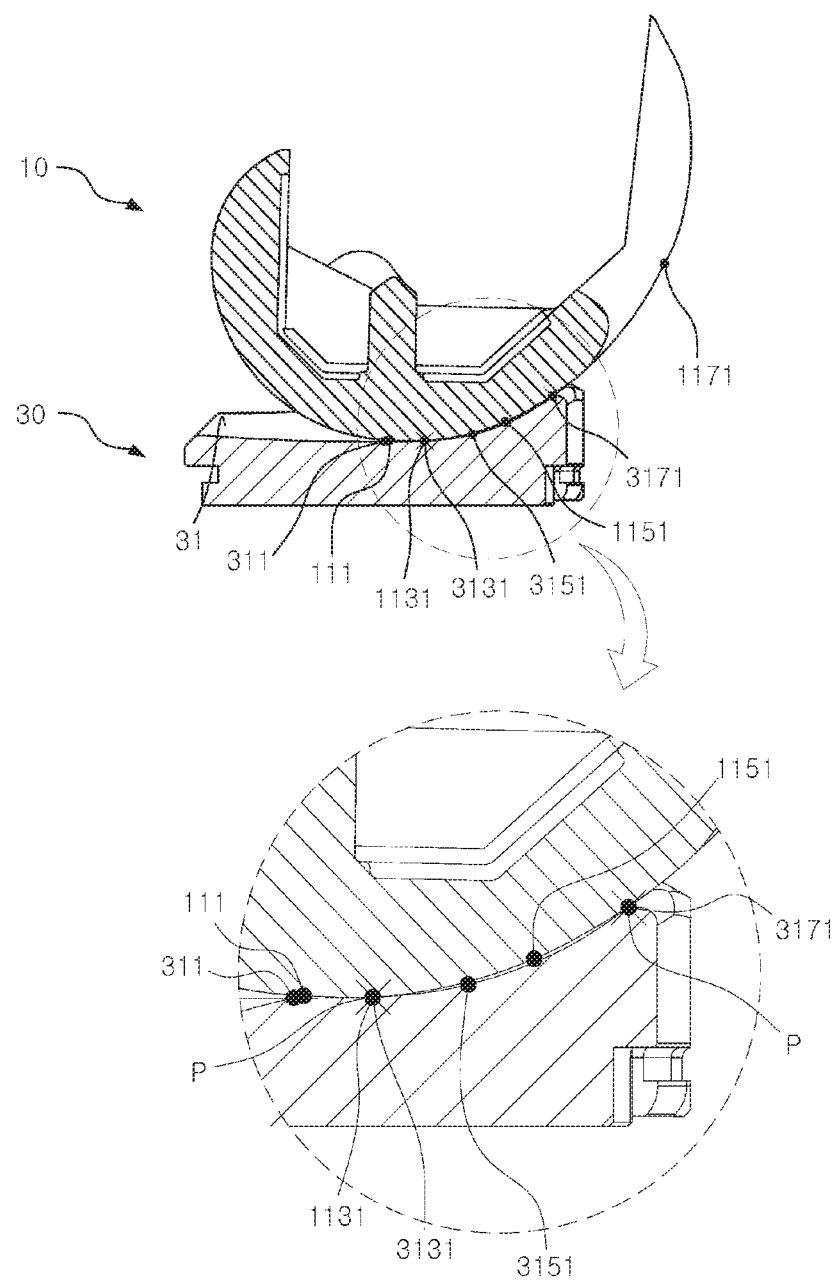
FIG. 14 is a view showing contact points that prevent hyperextension of a knee joint implant according to an embodiment of the present disclosure.

FIG. 13 is a view showing contact points in the extended state of a knee joint implant according to an embodiment of the present disclosure, and FIG. 14 is a view showing contact points that prevent hyperextension of a knee joint implant according to an embodiment of the present disclosure. Now, descriptions will be made with reference to FIGS. 13 and 14.

When a patient stands upright, the knees are extended, and at this time, the lowermost point 111 of the femoral component 10 is aligned with the lowermost point 311 of the bearing component 30 so as to be brought into single-point contact P therewith, as illustrated in FIG. 13.

In this situation, when a patient who has undergone a TKR operation performs an action such as lifting the forefoot from the floor so as to descend stairs, the extended knee tends to be hyperextended.

At this time, the femoral component 10 slides on the bearing component 30, which is capable of being accomplished by the first section 113 and the fourth section 313, which are generally horizontal.

When the femoral component 10 slides, the lowermost point 111 of the femoral component 10 moves toward the anterior side with respect to the lowest point 311 of the bearing component 30, as illustrated in FIG. 14. The end 1131 of the first section 113 may form a contact point P with the end 3131 of the fourth section 313, and at this time, the third section 117 of the femoral component 10 forms another contact point P with the end 3171 of the sixth section 317 of the bearing component 30, whereby, when the extended knee is about to be hyperextended, the condyle 11 of the femoral component 10 and the articular surface 31 of the bearing component 30 comes into two-point contact P with each other, so that further hyperextension can be prevented.

The foregoing detailed description illustrates the present disclosure. In addition, the foregoing description is intended to illustrate and explain embodiments of the present disclosure, and the present disclosure may be used in various other combinations, modifications, and environments. That is, it is possible to change or modify the present disclosure within the scope of the concept of the present disclosure disclosed in this specification, within the scope equivalent to the above-described contents, and/or within the scope of the skill or knowledge in the art. The embodiments described above are intended to illustrate the best mode for carrying out the technical idea of the present disclosure, and various modifications required for specific applications and uses of the present disclosure are also possible. Therefore, the detailed description of the present disclosure is not intended to limit the present disclosure to the disclosed embodiments. In addition, the appended claims should be interpreted as covering other embodiments as well.

What is claimed is:

1. A knee joint implant that prevents hyperextension, the knee joint implant comprising:
    a femoral component having a convex condyle with an anterior side, the convex condyle having an anterior surface with reference to a lowermost point of the convex condyle, the anterior surface having different curvature radii in respective sections thereof, the anterior surface comprising:
        a first section having a first curvature radius from the lowermost point of the condyle and extending toward the anterior side by a first angle from a center of the first curvature radius;
        a second section having a second curvature radius from an end of the first section and extending toward the anterior side by a second angle from a center of the second curvature radius; and
        a third section having a third curvature radius from an end of the second section and extending toward the anterior side by a third angle from a center of the third curvature radius, wherein the first curvature radius, the second curvature radius, and the third curvature radius are each different from each other; and
    a bearing component having a concave articular surface with an anterior side, the femoral component being configured to slide toward the anterior side of the concave articular surface of the bearing component and be brought into contact with the articular surface at a plurality of points.

2. The knee joint implant of claim 1, wherein the first curvature radius is larger than the second curvature radius.

3. The knee joint implant of claim 2, wherein the third curvature radius is smaller than the first curvature radius and larger than the second curvature radius.

4. The knee joint implant of claim 1, wherein the first angle is smaller than the second angle.

5. A knee joint implant that prevents hyperextension, the knee joint implant comprising:
    a bearing component having a concave articular surface with an anterior side, the concave articular surface having an anterior surface with reference to a lowermost point of the concave articular surface, the anterior surface having different curvature radii in respective sections thereof, the anterior surface comprising:
        a fourth section having a fourth curvature radius from the lowermost point of the articular surface and extending toward the anterior side by a fourth angle from a center of the fourth curvature radius;

a fifth section having a fifth curvature radius from an end of the fourth section and extending toward the anterior side by a fifth angle from a center of the fifth curvature radius; and a sixth section having a sixth curvature radius from an end of the fifth section and extending toward the anterior side by a sixth angle from a center of the sixth curvature radius, wherein the fourth curvature radius, the fifth curvature radius, and the sixth curvature radius are each different from each other;

a femoral component having a condyle, the femoral component being configured to slide toward the anterior side of the concave articular surface of the bearing component and be brought into contact with the articular surface at a plurality of points formed in the fourth section and the sixth section.

6. The knee joint implant of claim 5, wherein the fourth curvature radius is larger than the fifth curvature radius.

7. The knee joint implant of claim 6, wherein the sixth curvature radius is smaller than the fourth curvature radius and larger than the fifth curvature radius.

8. The knee joint implant of claim 5, wherein the fourth angle is smaller than the fifth angle.

9. A knee joint implant that prevents hyperextension, the knee joint implant comprising:

a femoral component having a convex condyle with an anterior side, the convex condyle having an anterior surface with reference to a lowermost point of the convex condyle, the anterior surface having different curvature radii in respective sections thereof; and a bearing component having a concave articular surface with an anterior side, the concave articular surface having an anterior surface with reference to a lowermost point of a concave articular surface, the anterior surface having different curvature radii in respective sections thereof, wherein the anterior surface of the femoral component comprises:

a first section having a first curvature radius from the lowermost point of the condyle and extending toward the anterior side of the condyle by a first angle from a center of the first curvature radius;

a second section having a second curvature radius from an end of the first section and extending toward the anterior side of the condyle by a second angle from a center of the second curvature radius; and a third section having a third curvature radius from an end of the second section and extending toward the anterior side of the condyle by a third angle from a center of the third curvature radius, wherein the first curvature radius, the second curvature radius, and the third curvature radius are each different from each other;

wherein the anterior surface of the bearing component comprises:

a fourth section having a fourth curvature radius from a lowermost point of the articular surface and extending toward the anterior side of the articular surface by a fourth angle from a center of the fourth curvature radius;

a fifth section having a fifth curvature radius from an end of the fourth section and extending toward the anterior side of the articular surface by a fifth angle from a center of the fifth curvature radius; and a sixth section having a sixth curvature radius from an end of the fifth section and extending toward the anterior side of the articular surface by a sixth angle from a center of the sixth curvature radius, wherein the fourth curvature radius, the fifth curvature radius, and the sixth curvature radius are each different from each other;

the femoral component and the bearing component being configured such that the condyle can slide toward the anterior side of the concave articular surface of the bearing component and be brought into contact with the articular surface at a plurality of points.

10. The knee joint implant of claim 9, wherein:

the first curvature radius is smaller than the fourth curvature radius, the second curvature radius is larger than the fifth curvature radius, and the third curvature radius is smaller than the sixth curvature radius.

11. The knee joint implant of claim 9, wherein the first section has an area that is smaller than an area of the fourth section.

* * * * *